United States Patent
Lee et al.

(10) Patent No.: US 6,683,452 B2
(45) Date of Patent: Jan. 27, 2004

(54) MAGNETIC FLUX DENSITY APPARATUS FOR, E.G., DETECTING AN INTERNAL CRACK OF A METAL OR A SHAPE OF THE METAL

(75) Inventors: Jin-yi Lee, Gimhae (KR); Won-ha Choi, Gimhae (KR); Min-soo Kim, Busan (KR); Dae-jung Kim, Busan (KR); Moon-phil Kang, Busan (KR)

(73) Assignee: Lacomm Co., Ltd. (KR)

( * ) Notice: Subject to any disclaimer, the term of this patent is extended or adjusted under 35 U.S.C. 154(b) by 0 days.

(21) Appl. No.: 09/997,258

(22) Filed: Nov. 30, 2001

(65) Prior Publication Data

US 2002/0101234 A1 Aug. 1, 2002

Related U.S. Application Data

(63) Continuation-in-part of application No. PCT/KR01/00999, filed on Jun. 12, 2001.

(30) Foreign Application Priority Data

Jul. 26, 2000 (KR) .............................................. 00-43130

(51) Int. Cl.$^7$ ................................................ G01N 27/72
(52) U.S. Cl. .................... 324/240; 324/67; 324/220; 324/242; 324/235; 324/260; 324/263; 324/329; 324/345; 324/750; 340/551
(58) Field of Search ................................ 324/240, 229, 324/230, 241, 262, 238, 209, 263, 220, 260, 67, 329, 345, 235; 340/551

(56) References Cited

U.S. PATENT DOCUMENTS

| | | | | | |
|---|---|---|---|---|---|
| 3,532,969 | A | * | 10/1970 | McCullough | 324/229 |
| 4,806,863 | A | * | 2/1989 | White | 324/238 |
| 5,394,083 | A | * | 2/1995 | Jiles | 324/223 |
| 5,574,365 | A | * | 11/1996 | Oyama et al. | 324/207.24 |
| 5,617,024 | A | * | 4/1997 | Simpson et al. | 324/209 |
| 5,747,989 | A | | 5/1998 | Kimura et al. | |
| 5,847,562 | A | * | 12/1998 | Fulton et al. | 324/229 |
| 5,942,894 | A | * | 8/1999 | Wincheski et al. | 324/220 |
| 6,317,048 | B1 | * | 11/2001 | Bomya et al. | 340/573.1 |
| 6,424,149 | B1 | | 7/2002 | Takahashi | |

FOREIGN PATENT DOCUMENTS

| | | | |
|---|---|---|---|
| JP | 55071064 | * | 5/1980 |
| JP | 11-311617 A | | 11/1999 |
| JP | 2001-133440 A | | 5/2001 |

* cited by examiner

*Primary Examiner*—N. Le
*Assistant Examiner*—Reena Aurora
(74) *Attorney, Agent, or Firm*—Rothwell, Figg, Ernst & Manbeck; Stephen H. Parker

(57) ABSTRACT

A display apparatus of magnetic flux density for detecting an internal crack of a metal or a shape of the metal includes a three-dimensional magnetic flux focusing unit installed near the metal, for concentrating magnetic flux generated by the metal, a magnetic flux density measurement unit installed near the magnetic flux focusing unit, for measuring changes in magnetic flux density concentrated by the magnetic flux focusing unit, and a display unit electrically connected with the magnetic flux measurement unit, for real-time displaying and storing changes in the magnetic flux density.

18 Claims, 10 Drawing Sheets

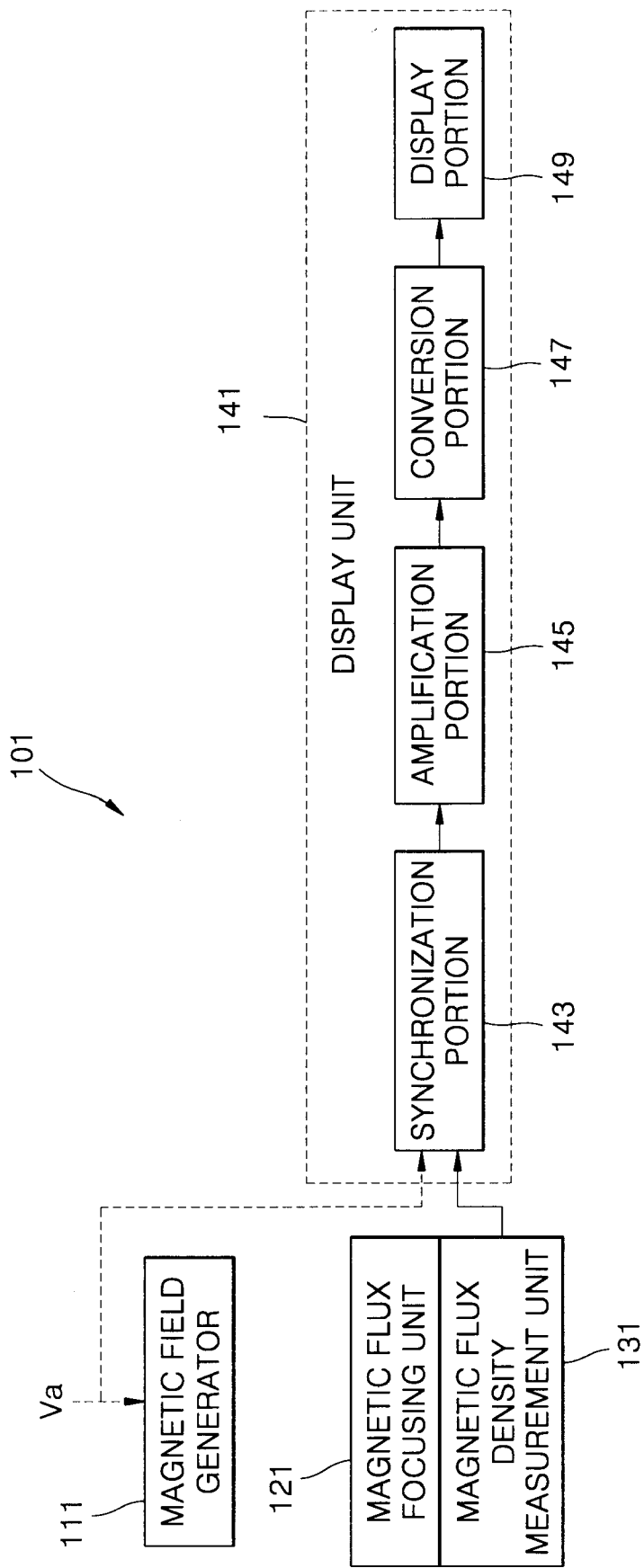

MAGNETIC FLUX DENSITY APPARATUS FOR, E.G., DETECTING AN INTERNAL CRACK OF A METAL OR A SHAPE OF THE METAL

CROSS REFERENCE TO RELATED APPLICATIONS

This application is a Continuation-in-part of PCT International Application Number PCT/KR01/00999, filed on Jun. 12, 2001, which claims priority to Korean Patent Application Number 00-43130, filed on Jul. 26, 2000, and which has not been published in the English language.

BACKGROUND OF THE INVENTION

1. Field of the Invention

The present invention is related to a display apparatus of magnetic flux density, especially designed to visualize in a real time the change of magnetic flux density.

2. Description of the Related Art

Any machinery or structure can be effectively used for an extended using time while its safety is guaranteed with sufficient reliability and within the allowed economic efficiency. For this, a nondestructive testing technology, i.e., the quality management to eliminate the goods out-of-specifications in each manufacturing processes, the quality control of materials, the repair inspections to check the occurrence of dangerous defects which the goods are being used by customers is specially important. Among them, the magnetic method using magnetic phenomena and the eddy current method are effective to detect cracks on the surface and near the surface of materials. However, an automatic scanning system must be used to quantitatively measure the distribution of magnetic flux density.

Also, it is necessary to get an enough lift-off to measure the magnetic flux density under the high-temperature conditions or contaminated environments, which becomes the reason for low sensitivity of sensors and, it is also necessary to measure the magnetic flux density with limited sensing areas for large scaled objects.

On the other hand, metal detection doors are usually used to prohibit people from carrying in arms at airports and at places where securities are required. Since the conventional metal detection doors can only check the existence of metallic objects in a limited region, it is difficult to discern hand-held phones, keys, and coins from the arms. Therefore, to visualize the shapes of metallic objects, it is necessary to use X-ray equipment, the metal detection doors and metal detectors at the same time that accompanies burdens in time and cost.

To detect mines or metals buried or imbedded under the ground or on the wall, the metal detection equipment by electromagnetic method is usually used. It is necessary to visualize the distribution or data of magnetic flux density in a large area quantitatively and in a fast manner to discern magnetic particles in the sand, metallic debris, coins and mines.

However, in many cases, the lift-off of sensors from the mines or metals is large enough so that the sensitivity of magnetic sensors is degraded, moreover, it is necessary to measure large area because the area to be measured becomes large with increasing of lift-off.

As described above, in applying the electromagnetic methods to nondestructive tests, metal detection doors and metal detectors, there is no such an apparatus that reduces the effect of lift-off, does not require any space-limited automatic scanning systems, but visualizes the distributed magnetic flux density over a large area quantitatively in a fast manner by using magnetic field sensors with limited area.

Even there is a method using a ferromagnetic flat panel to focus magnetic flux to measure magnetic flux density with high sensitivity, it is necessary to solve the problem of residual magnetization or magnetic hysterises phenomenon in a ferromagnetic flat panel.

In addition to those, it is difficult to manufacture three-dimensional shape of metal because of mechanical characteristics of metals, it is necessary to demagnetizing, and it is not easy to reuse for another shape.

SUMMARY OF THE INVENTION

To solve the above-described problems, it is an object of the present invention to provide a display apparatus of magnetic flux density that visualizes and measures the distribution of magnetic flux density over a large area quantitatively in a real time with small spatial limitation.

To achieve the above object, there is provided a display apparatus of magnetic flux density for detecting an internal crack of a metal or a shape of the metal comprising a three-dimensional magnetic flux focusing unit installed near the metal, for concentrating magnetic flux generated by the metal, a magnetic flux density measurement unit installed near the magnetic flux focusing unit, for measuring changes in magnetic flux density concentrated by the magnetic flux focusing unit, and a display unit electrically connected with the magnetic flux measurement unit, for real-time displaying and storing changes in the magnetic flux density.

It is preferred in the present invention that the magnetic flux focusing unit comprise a container having magnetic fluid.

It is preferred in the present invention that the magnetic flux focusing unit comprises a ferromagnetic material.

It is preferred in the present invention that the magnetic flux focusing unit comprises an absorber of magnetic fluid.

It is preferred in the present invention that the absorber is either one of paper or sponge.

It is preferred in the present invention that the outer shape of the magnetic flux focusing unit is one of circle, rectangle or polygon.

It is preferred in the present invention that the magnetic flux focusing unit has the outer shape of the combination of circle, rectangle, or polygon.

It is preferred in the present invention that the magnetic sensor is a Hall sensor comprising a plurality of Hall effect semiconductor chips.

It is preferred in the present invention that the Hall sensor comprises an insulator on which the chips are arranged to a predetermined distance.

It is preferred in the present invention that the display apparatus of magnetic flux density comprises an additional magnetic field generator to magnetize the magnetic materials set up near the magnetic materials.

It is preferred in the present invention that the magnetic field generator comprise a conductor for generating a magnetic field when a current flows.

It is preferred in the present invention that the magnetic field generates is set up on the security door, and the door can detect whether the people walking through it has the magnetic materials or not if the magnetic lens and the magnetic flux density measurement device are set up on one side of the door.

It is preferred in the present invention that the metal is a line patterned on the printed circuit board, magnetic fields are generated around the printed circuit board when currents flow through the lines, and the display device can display the currents flowing through the lines.

It is preferred in the present invention that the meal is buried under the ground and the metal is magnetized by the terrestrial magnetism.

BRIEF DESCRIPTION OF THE DRAWINGS

The above object and advantages of the present invention will become more apparent by describing in detail preferred embodiments thereof with reference to the attached drawings in which:

FIG. 1 shows the block diagram about a display apparatus of magnetic flux density of this invention;

FIG. 6a is an example into security door by a display apparatus of magnetic flux density illustrated in the FIG. 1;

FIG. 6b is the magnified drawing for the magnetic flux concentrating unit and magnetic flux density measuring unit of FIG. 6a;

DETAILED DESCRIPTION OF THE INVENTION

Figure 2A:
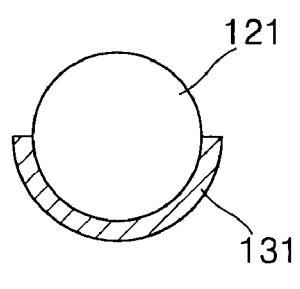
FIGS. 2a through 2d are the drawings that show a variety of shapes about the magnetic flux focusing unit illustrated in the FIG. 1.

Referring to the following attached drawings, the desirable applied examples for this invention are fully described.

FIG. 1 is the block diagram that shows a display apparatus of magnetic flux density by this invention. Referring to FIG. 1, a display apparatus of magnetic flux density 101 includes magnetic field generator 111, magnetic flux focusing unit 121, magnetic flux density measuring unit 131, and a display apparatus 141.

The magnetic field generator 111 magnetizes the object "metal not illustrated here)" by generating magnetic field. The magnetic field generator 111 is consisted of conductor that generates the magnetic field when the electric current supplied form the outside flows, for example coil, metal plates, and etc.

The magnetic flux focusing unit is installed near the metal and concentrates the magnetic flux generated from the metal. The magnetic flux focusing unit 121 has a three-dimensional shape and can be formed with the plural number.

The magnetic flux density measuring unit 131 is installed on the surface of the magnetic flux focusing unit 121 and consisted of numerous magnetic sensors in order to measure the variation of the concentrated magnetic flux density. See FIG. 8 to get the full description of the magnetic sensor.

The display unit 141 is connected to the magnetic flux density measuring unit 131 electrically and stores the signals generated from the magnetic flux density measuring unit and displays the shape of the metal or the internal cracks of the metal visually by analyzing the variation of the magnetic flux density.

The display apparatus 141 possesses synchronizing part 143, amplifying part 145, and indicating part 149. For the power supply that supplies the electric current of the magnetic field generator 111, when it uses the AC power supply, the phase of the magnetic field generator 111 and the output of the magnetic flux density measuring unit 131 are synchronized by the synchronizing part 143.

The magnetic flux density distribution, which is converted to the electrical signal by the magnetic flux density measuring unit 131, is inputted into the converting part 147 through the amplifying part 145 that converts and amplifies the same number of electric signals by the magnetic flux density measuring unit 131. The converting part 147 converts the analog signals generated from the magnifying part 145 into the digital signal and deliver them to the indicating part 149. The indicating part 149 stores the inputted signals and displays the magnetic flux density distribution visually.

The display apparatus of magnetic flux density 101 measures and indicates the wide area of the magnetic flux density distribution quantitatively by the limited area of the magnetic flux density measuring unit 131 to apply the magnetic method to NDT Non Destructive Testing for industrial use or metal detection systems.

FIGS. 2a through FIG. 2d are the drawings that show various types of the magnetic flux focusing units 121 illustrated in FIG. 1.

Referring to FIG. 2a, the magnetic flux focusing unit 121 is composed of circle and the magnetic flux density measuring unit 131 is attached on the lower sphere of the magnetic flux focusing unit 121.

Figure 2B:
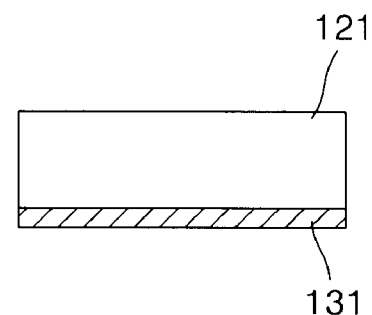

Referring to FIG. 2b, the magnetic flux focusing unit 121 is composed of rectangle and the magnetic flux density measuring unit 131 is attached on the lower part of the magnetic flux focusing unit 121.

Figure 2C:
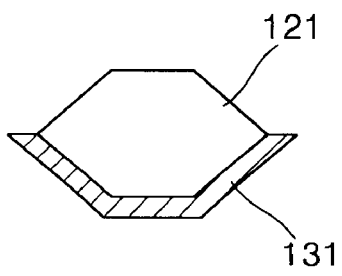

Referring to FIG. 2c, the magnetic flux focusing unit 121 is composed of polygon and the magnetic flux density measuring unit 131 is attached on the lower side of the magnetic flux focusing unit 121.

Figure 2D:
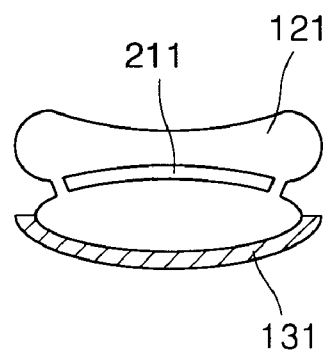

Referring to FIG. 2d, the magnetic flux focusing unit 121 combines the two magnetic flux focusing units 121 that makes an interval 211 and it enables the air to pass through the interval, the magnetic flux density measuring unit 131 is attached on the lower part of the magnetic flux focusing unit 121.

The magnetic flux focusing unit 121 can be composed of the mixed types by the shapes illustrated in the FIG. 2a or FIG. 2d.

The magnetic flux focusing unit 121 illustrated in FIGS. 2a through FIG. 2d also can be composed of an absorber that has the magnetic fluid or the vessel that contains the magnetic fluid inside. The absorber can be made of either paper or sponge. Paper or sponge makes the three-dimensional shape easy by penetrating the magnetic fluid into the paper or sponge, and etc. Using the magnetic fluid as the magnetic flux focusing unit 121 makes reuse possible without the need of mechanical engineering work in comparison with metal. Also, the realization of any shape can be possible by putting this into the easily moldable plastic vessels. Especially, the characteristic of magnetic fluid is that it has very few magnetic hysterisis.

Also, the magnetic flux focusing unit 121 can be composed of ferromagnetic materials, for example steel, cobalt, nickel or those alloys.

Figure 3:
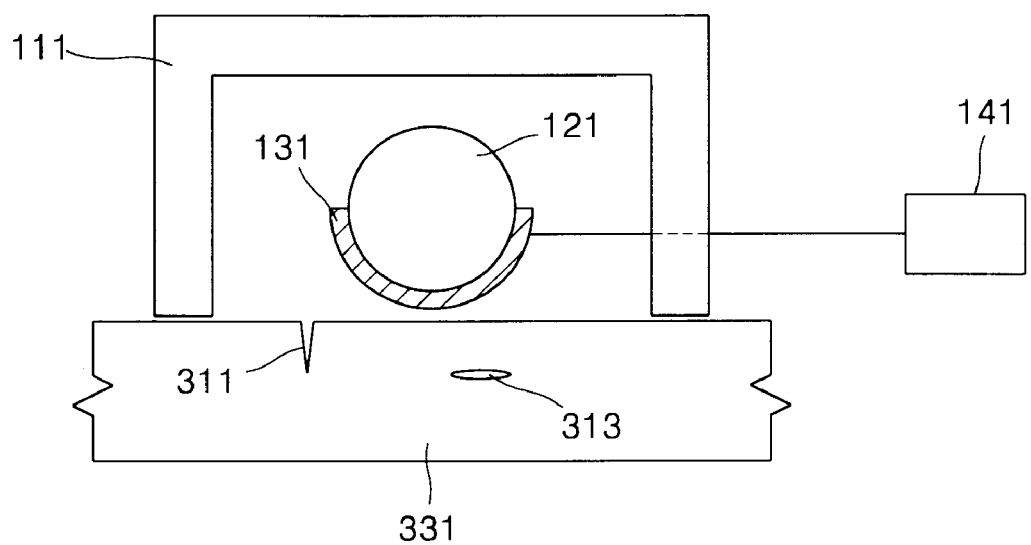
FIG. 3 is the cross-sectional view of a display apparatus of magnetic flux density illustrated in the FIG. 1 that shows an example by magnetic nondestructive inspection for ferromagnetic structure.

FIG. 3 is the cross-sectional view of a display apparatus of magnetic flux density 101 illustrated in FIG. 1 that shows an example for the magnetic detection of ferromagnetic structure. Referring to FIG. 3, the magnetic field generator 111 is installed on the upper part of the object 331, ferromagnetic structure and magnetizes the ferromagnetic structure. And, the leakage magnetic flux is generated from the surface crack 311 or internal crack 313 that are latent in the ferromagnetic structure. Being measured by the magnetic flux density measuring unit 131 after being concentrated by the magnetic flux focusing unit 121, the leakage magnetic flux makes the spatial distribution of the magnetic flux density measurable.

Figure 4:
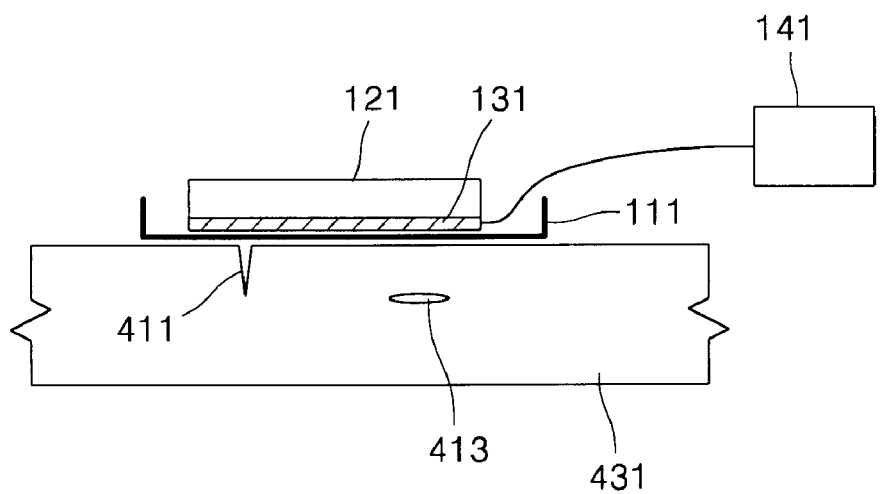
FIG. 4 is the cross-sectional view of a display apparatus of magnetic flux density illustrated in the FIG. 1 that shows an example by eddy current nondestructive inspection for paramagnetic structure.

FIG. 4 is the cross-sectional view of a display apparatus of magnetic flux density 101 illustrated in FIG. 1 that shows an example for the eddy current detection of the paramagnetic structure. Referring to FIG. 4, the magnetic field generator 111 is installed in the eddy current detection of the object. The magnetic field generator 111 generates induced current on the surface or below of the paramagnetic structure by the steady direction of sheet current or eddy current.

Then the magnetic flux generates on the surface of the paramagnetic structure and towards the perpendicular direction by the internal crack 413 or the surface crack 411 of the ferromagnetic structure. Concentrated with the magnetic flux focusing unit 121 and measured by the magnetic flux density measuring unit 131, this magnetic flux enables the spatial distribution of the magnetic flux density to be measured quantitatively.

Figure 5:
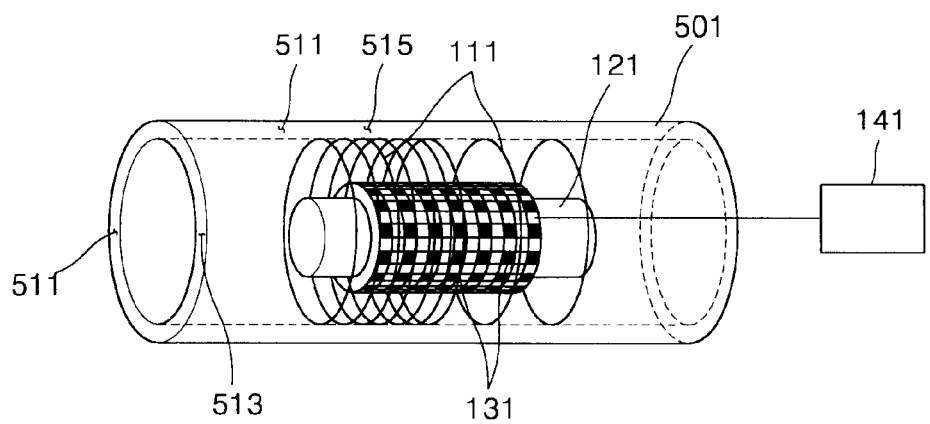
FIG. 5 is the schematic illustration for a display apparatus of magnetic flux density illustrated in the FIG. 1 that shows an example for detecting the cracks inside tubes.

FIG. 5 is the schematic illustration of a display apparatus of magnetic flux density illustrated in the FIG. 1 that shows an example for detecting the cracks inside tubes. Referring to FIG. 5, the magnetic field generator 111, magnetic flux focusing unit 121 or magnetic flux density measuring unit 131 is installed in the tube 501. The magnetic field generator 111 is installed in the inside or outside part of the tube 501 and magnetizes the tube 501. Then the leakage magnetic flux generates by the existence of inside crack 511, outside crack 513, or internal crack 515. Concentrated by the magnetic flux focusing unit 121 and measured by the magnetic flux density measuring unit 131, the leakage magnetic flux enables the spatial distribution of the magnetic flux density to be measured quantitatively.

Figures 6A, 6B:
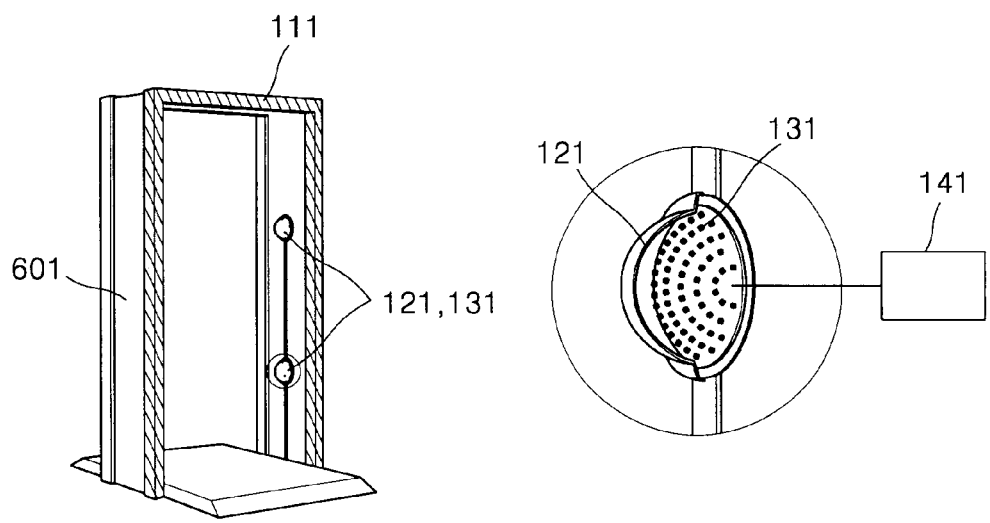

FIG. 6a is an example into security door by a display apparatus of magnetic flux density illustrated in the FIG. 1, FIG. 6b is the large drawing for the magnetic flux focusing unit or magnetic flux density measuring unit of FIG. 6a. Referring to FIG. 6a or FIG. 6b, the magnetic field generator 111, magnetic flux focusing unit 121 or magnetic flux density measuring unit 131 is installed in the security door 601. The variation of the magnetic flux density of the metal objects possessed by the passenger who passes through the door 601 is induced by the magnetic field generated from the magnetic field generator 111. The variation of the magnetic flux density, concentrated by the magnetic flux focusing unit 121 and measured by the magnetic flux density measuring unit 131, makes the spatial distribution of the magnetic flux density measurable quantitatively.

Figure 7:
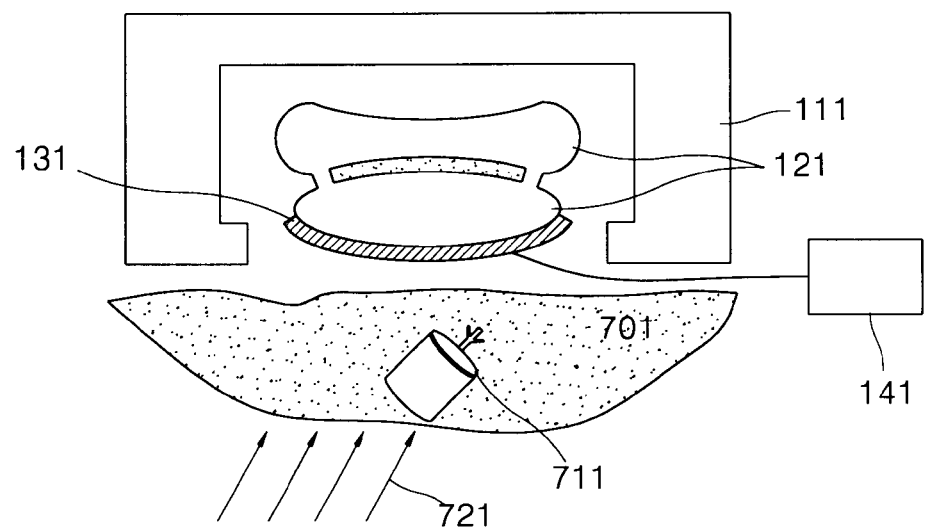
FIG. 7 is the cross-sectional view of a display apparatus of magnetic flux density illustrated in the FIG. 1 that shows an example for detecting underground metals.

FIG. 7 is the cross-sectional view of a display apparatus of magnetic flux density 101 illustrated in the FIG. 1 that shows an example for detecting underground metals. Referring to FIG. 7, the object "metal 711" buried under the ground 701 generates magnetic flux by the terrestrial magnetism. The variation of the magnetic flux density, concentrated by the magnetic flux focusing unit 121 and measured by the magnetic flux density measuring unit 131, makes the spatial distribution of the magnetic flux density measurable quantitatively.

Figure 8:
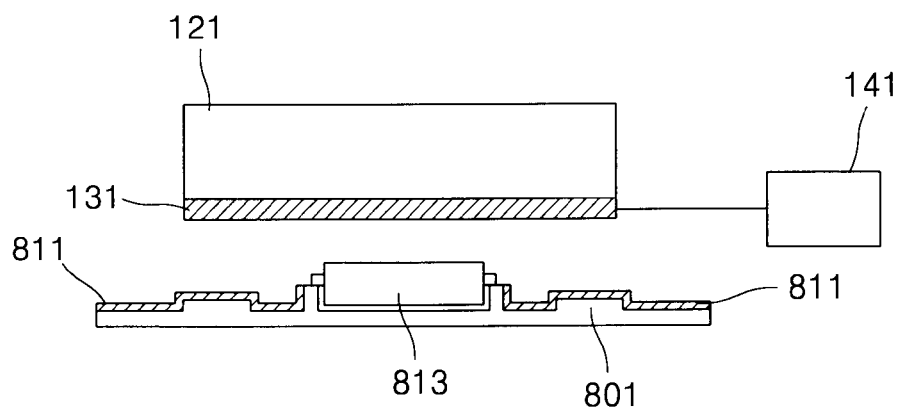
FIG. 8 is the cross-sectional view of a display apparatus of magnetic flux density illustrated in the FIG. 1 that shows an example for measuring the electric density distribution on the printed circuit board.

FIG. 8 is the cross-sectional view of a display apparatus of magnetic flux density illustrated in the FIG. 1 that shows an example for measuring the electric density distribution on the printed circuit board. Referring to FIG. 8, the magnetic flux focusing unit 121 or magnetic flux density measuring unit 131 is installed on the printed circuit board 813. The wiring 811 and semi-conducting apparatus 813 is concentrated on the upper side of the printed circuit board 801. The current flowing in the wiring generates the magnetic flux by the law of electromagnetic induction and then the variation of the magnetic flux density occurs by the variation of the current density. The variation of the magnetic flux density, concentrated by the magnetic flux focusing unit 121 and measured by the magnetic flux density measuring apparatus 131, makes the spatial distribution of the magnetic flux density measurable quantitatively, so the current density flowing in the wiring 811 can be estimated.

Figure 9:
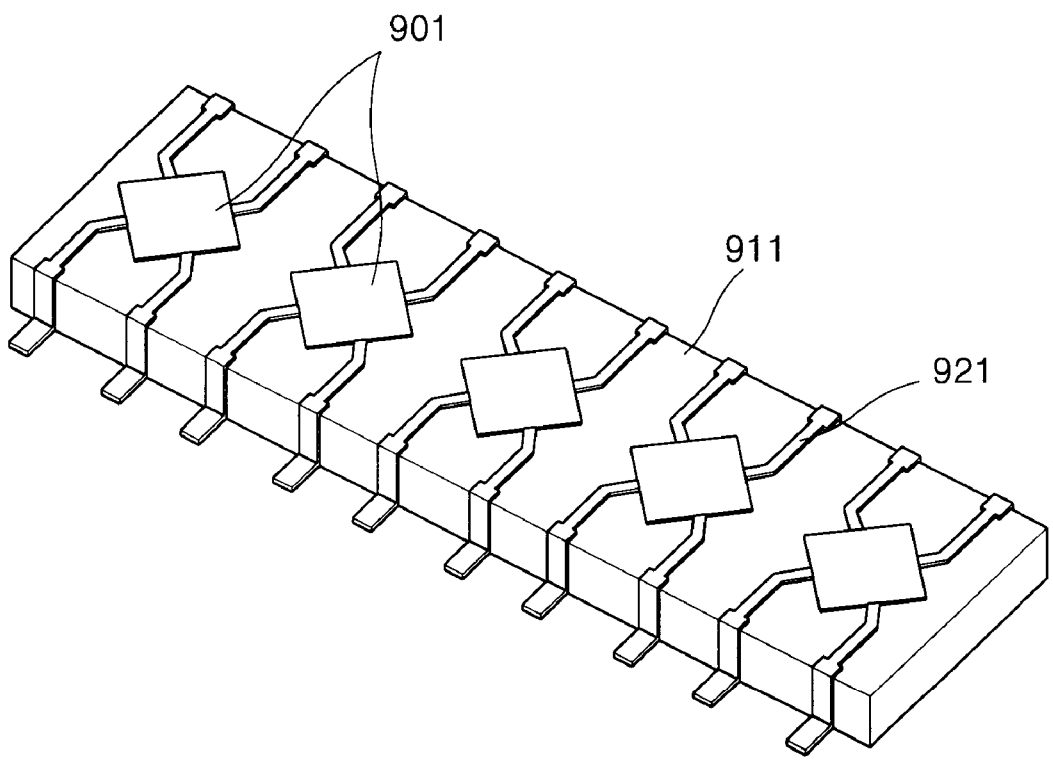
FIG. 9 is an example of the magnetic sensors illustrated in the FIG. 1.

FIG. 9 is an example of the magnetic sensors illustrated in the FIG. 1. Magnetic sensor is Hall sensors that is consisted of a number of semi-conductor chips 901 with the Hall effect in order to measure the variation of magnetic flux density concentrated by the magnetic flux focusing unit 121. Referring to FIG. 9, Hall sensors are consisted of insulator 911, for example plastic plate with the numerous semi-conductor chips that are arrayed regularly with the fixed interval. Generally, semi conductor chips are manufactured by the technology of semi conductor integrated circuit, Hall sensors are manufactured through several manufacturing processes such as sawing process that separates numerous semi conductor chips formed on the wafer into each one, die attach process that attaches the separated semi conductor chips to the lead frame 921, wire bonding process that connects the semi conductor chips to the lead frame 921 by using wire electrically, and molding process that packages the lead frame 921.

Through these processes, the interval among the Hall effect semi conductor chips 901 ranges from tens of□μm□to hundreds of□μm□. So, the Hall sensors can measure the variation of the magnetic flux density closely by including numerous semi conductor chips 901.

Table 1 shows permeability and density by the materials for the magnetic flux focusing unit 121.

TABLE 1

| Material | Air | Magnetic fluid | Iron | Silicon steel | Anisotropic silicon steel |
| --- | --- | --- | --- | --- | --- |
| Initial Permeability | 1 | 60 | 250 | 500 | 1500 |
| Density□Kg/m³□ | 1.293 | 1157 | 7880 | 7650 | 7600 |

Figure 10:
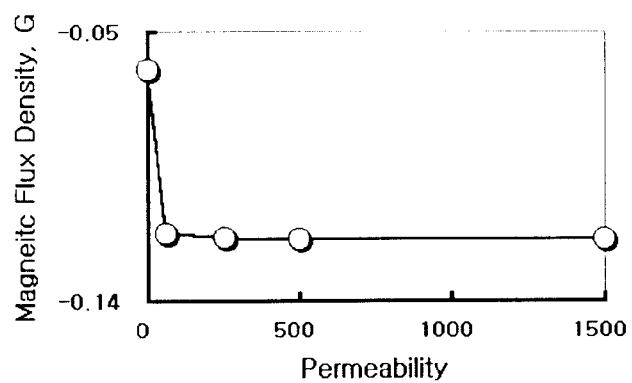
FIG. 10 is the graph that shows the numerically analyzed result that how the maximum magnetic flux density on the surface of circular ferromagnetic material within homogeneous magnetic field changes by the variation of permeability.

FIG. 10 is the graph that shows the numerically analyzed result that displays how the maximum magnetic flux density on the surface of circular ferromagnetic material of steady magnetic field changes by the variation of permeability. According to FIG. 1, we can see there is very little difference about the effect of the magnetic flux concentration in comparison with the considerable change of permeability as shown in FIG. 10. So to speak, about the effect of the magnetic flux concentration, we can get not only the effect of the magnetic flux concentration similar to that of materials with high permeability like anisotropic silicon steel even if we use the magnetic fluid excluding ferromagnetic metal but also the light weighted magnetic flux focusing unit 121 in case of the magnetic fluid as known from its density.

Figure 11:
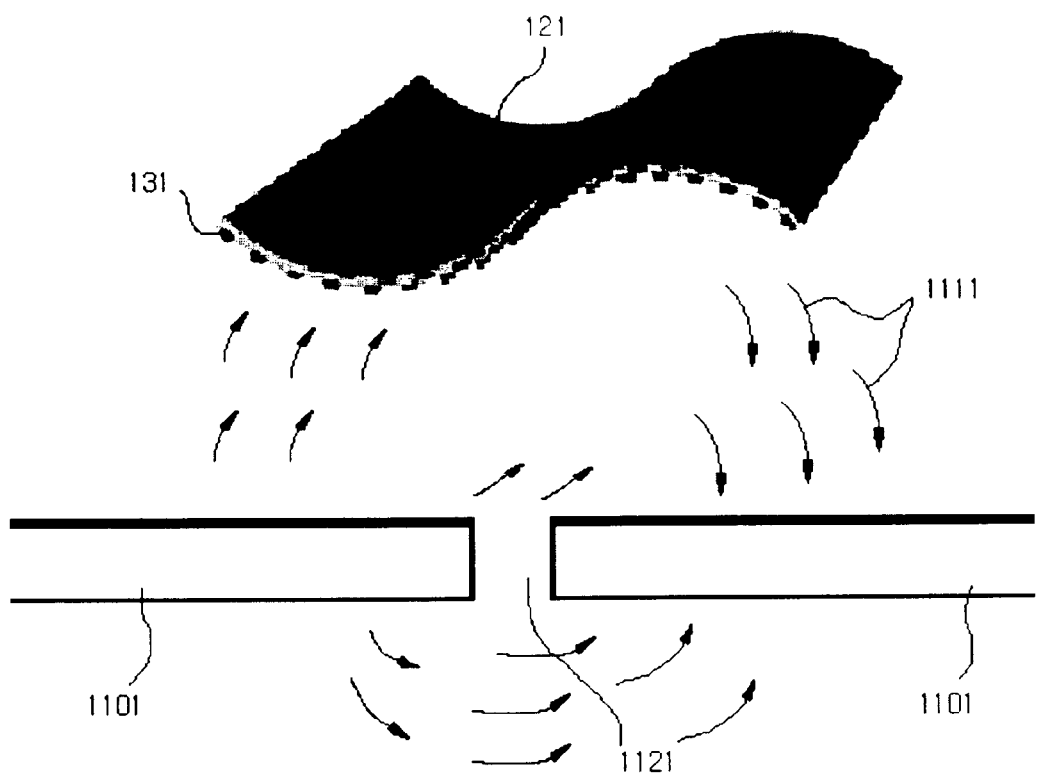
FIG. 11 is the drawing that illustrates a model to see how the leakage magnetic flux changes by the shape of the magnetic flux concentrating unit.

FIG. 11 is the drawing that illustrates a model to see how the leakage magnetic flux from the internal crack 1121 of the object 1101 changes by the surface shape of the magnetic flux focusing unit 121. When the surface shape of the magnetic flux focusing unit 121 is circular 2020, rectangle 2040, and polygon 2030, the magnetic flux density distribution concentrated in the normal direction on the surface of the magnetic flux focusing unit 121 is shown in FIG. 12.

Figure 12:
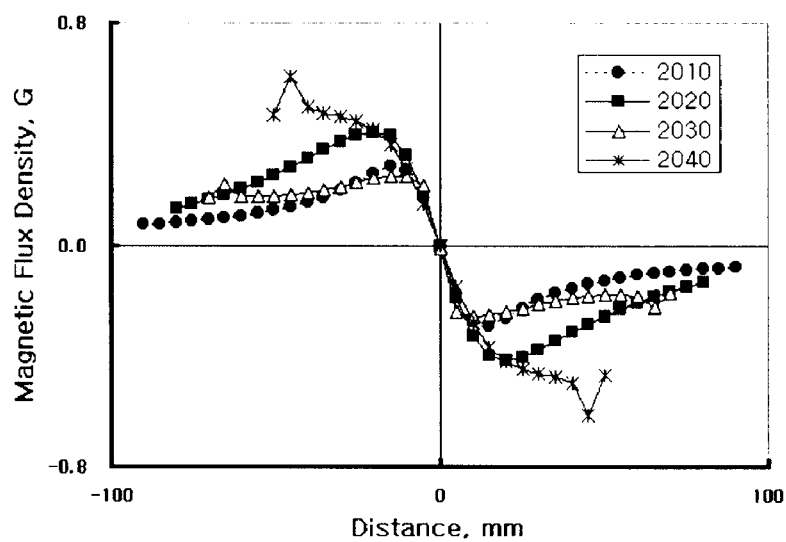
FIG. 12 is the graph that shows the analyzed result of the magnetic flux density distribution concentrated normally on the surface of circular, rectangle, and polygon magnetic flux focusing unit.

Reference numeral 2010 in FIG. 12 is to show the magnetic flux focusing unit 121 is nonexistent, the lift-off at this time is half the minimum lift-off from circular 2020, rectangle 2040, polygon 2030 magnetic flux focusing unit 121 to the object 1101 in FIG. 11. From this result, we can see that the effect of the magnetic flux concentration is much higher with 3-dimensional shape of ferromagnetic materials 2020, 2030, 2040 in comparison with the nonexistence of ferromagnetic materials 2010. Also, even though the distance from the original source of the magnetic flux to the measuring part of the magnetic flux density becomes wide, we can see it is possible to get the increasing effect of lift-off when the magnetic flux density measuring unit 131 is located on the surface of the magnetic flux focusing unit 121.

Figure 13:
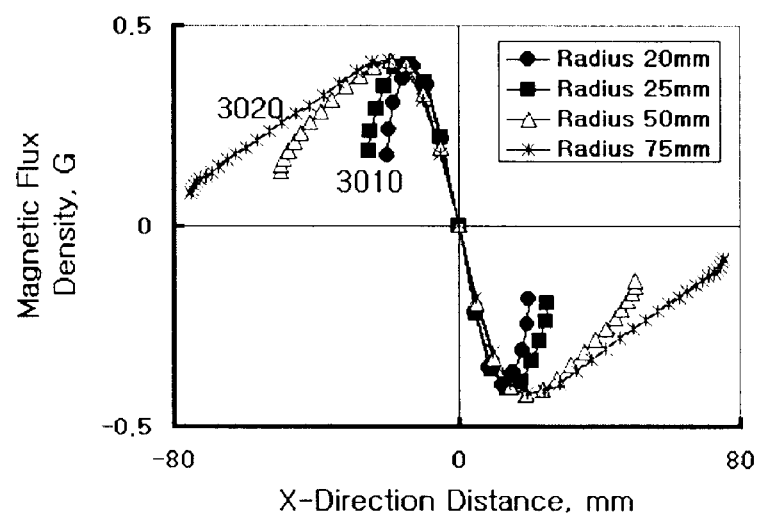
FIG. 13 is the graph that shows the analyzed result about the relation between the radius size and the magnetic flux density distribution when it comes to the circular magnetic flux focusing unit.

FIG. 13 is the relation between the radius size and the magnetic flux density distribution when it comes to the circular magnetic flux focusing unit 121 and shows the maximum magnetic flux density has very little difference. However, in case of the small radius 3010 comparing to the big one 3020, we can see the location of the maximum magnetic flux density is close to the crack that shows the display of the measuring area can be both increased and decreased by the radius of the circular magnetic flux focusing unit 121.

Figure 14:
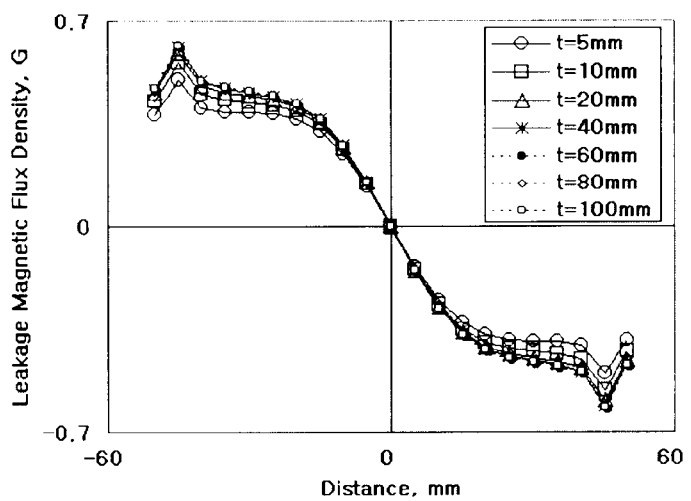
FIG. 14 is the graph that shows the relation between the thickness and the magnetic flux density distribution when it comes to the rectangle magnetic flux focusing unit.

FIG. 14 displays the magnetic flux density distribution on the surface of the rectangle magnetic flux focusing unit 121, we can see here that the thickness of the magnetic lens has no big influence on the effect of the magnetic flux focusing, so to speak, we can get enough effect of the magnetic flux concentration with thin magnetic lens.

Figure 15A:
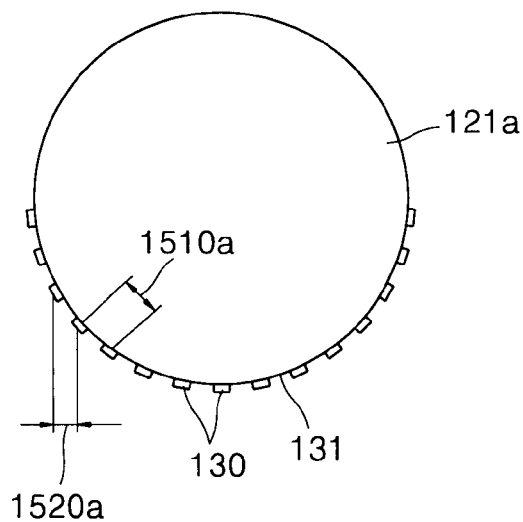
FIG. 15a is the drawing illustrated in case the magnetic flux density measuring unit is located on the curved surface.
Figure 15B:
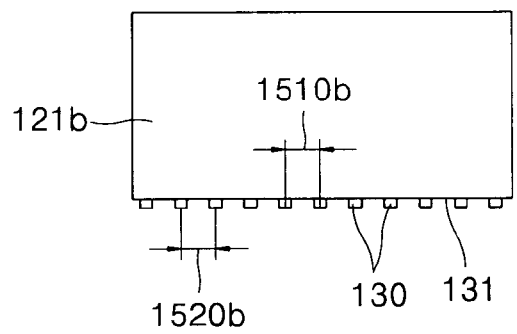
FIG. 15b is the drawing in case the magnetic flux density measuring unit is located on the level surface.

FIG. 15a is the drawing when the magnetic flux density measuring unit 131 is located on the curved surface, and FIG. 15b is the drawing when the magnetic flux density measuring unit 131 is located on the level surface. When the shape of the magnetic flux focusing unit is curved like the circle 12a and the interval 1510a between sensors close to the magnetic flux density measuring unit 131 located on the level surface is same with the interval 1510b of the magnetic flux density measuring unit 131 located on the level surface 121b, more magnetic flux density measuring unit 131 can be arrayed that means more spatial resolution because the interval between magnetic sensors 130 on the same spatial projecting plane as the interval 1520a in case of the curved like circle 121a, and etc is shorter than the interval 1520b located on the level surface 121b.

Figure 16A:
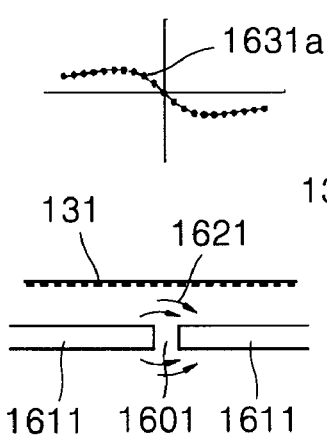
FIGS. 16a thorough 16c are the drawings that describe the magnetic flux density measuring unit arrayed on the surface of the magnetic flux focusing unit and in the magnetic flux focusing unit.

FIG. 16a shows that the leakage magnetic flux 1621 is generated near the defect 1601 by magnetizing the object 1611 with a defect 1601 and measure the magnetic flux density distribution 1631 a by two-dimensional or three-dimensional arrayed magnetic flux density measuring unit 131.

Figure 16B:
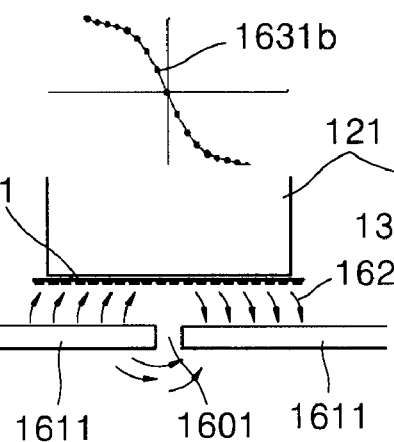

As shown in FIG. 16b, if you measure the magnetic flux density distribution 1631b by the two-dimensional magnetic flux density measuring unit 131 arrayed on the surface of the plate ferromagnetic magnetic flux focusing unit 121, the leakage magnetic flux 1601 is attracted to the magnetic flux focusing unit 121 because it has the property of being attracted to ferromagnetic materials.

Figure 16C:
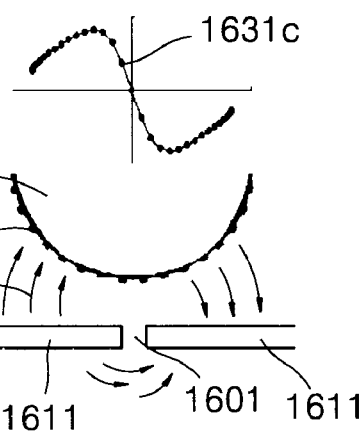

Referring to FIG. 16c, even though the magnetic flux is the same kind of ferromagnetic materials, the magnetic flux density distribution 1631c can amplify and control the measuring area as well by the shape or size of the magnetic flux focusing unit 121.

The magnetic flux on the surface is not overlapped each other and depends largely on the shape or size of ferromagnetic material because of its property of being attracted to ferromagnetic materials, so it is possible to amplify the signal and control the measurable area.

As mentioned above, when it comes to measuring the power of wide magnetic field two-dimensionally, it has no spatial limitation in comparison with the automatic scanning instrument and is possible to measure and display the magnetic flux density quantitatively within a short time. And it can secure enough lift-off to measure the magnetic flux density generated from high-temperature and contaminated objects. Also it can measure and display the wide area of the magnetic flux density distribution by the limited area of the magnetic flux density measuring unit 131. Also, when using Hall effect semiconductor chips as the magnetic flux measuring unit 121, the interval of sensors can be ranged from tens of□μm□to hundreds of□μm□. And by using magnetic fluid as the magnetic flux focusing unit 121, it is possible to concentrate the magnetic flux, amplify the magnetic flux density, increase lift-off, reduce the weight, and realize the three-dimensional shape that controls the measuring area. Also the magnetic fluid that is used as the three-dimensional shape can be reused to another 3-dimensional shape. Also, when the magnetization by the magnetic field generator 111 is eliminated, there is no residual magnetization because of very small magnetic hysterisis.

This invention can be applied to NDT and metal detection that are using the electromagnetic principle. While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A display apparatus of magnetic flux density for detecting an internal crack of a metal or a shape of the metal comprising:
    a three-dimensional magnetic flux focusing unit installed near the metal, for concentrating magnetic flux generated by the metal;
    a magnetic flux density measurement unit installed near the magnetic flux focusing unit, for measuring changes in magnetic flux density concentrated by the magnetic flux focusing unit;
    a display unit electrically connected with the magnetic flux measurement unit, for real-time displaying and storing changes in the magnetic flux density; and
    wherein the magnetic flux focusing unit comprise a container having magnetic fluid.

2. The apparatus as claimed in claim 1, wherein the magnetic flux focusing unit comprises a ferromagnetic material.

3. The apparatus as claimed in claim 1, wherein the outer shape of the magnetic flux focusing unit is one of circle, rectangle or polygon.

4. The apparatus as claimed in claim 1, wherein the outer shape of the magnetic flux focusing unit is one of circle, rectangle, or polygon.

5. The apparatus as claimed in claim 1, wherein the magnetic sensor is a Hall sensor comprising a plurality of Hall effect semiconductor chips.

6. The apparatus as claimed in claim 5, wherein the Hall sensor comprises an insulator on which the chips are arranged to a predetermined distance.

7. The apparatus as claimed in claim 1, wherein the display apparatus of magnetic flux density comprises an additional magnetic field generator to magnetize the magnetic materials set up near the magnetic materials.

8. The apparatus as claimed in claim 7, wherein the magnetic field generator comprise a conductor for generating a magnetic field when a current flows.

9. The apparatus as claimed in claim 7, wherein the magnetic field generator is set up on a security door, and the door can detect whether the people walking through it has the magnetic materials or not if the magnetic lens and the magnetic flux density measurement device are set up on one side of the door.

10. The apparatus of claim 1, wherein the metal is a line patterned on the printed circuit board, magnetic fields are generated around the printed circuit board when currents flow through the lines, and the display device can display the currents flowing through the lines.

11. The apparatus as claimed in claim 1, wherein the metal is buried under the ground and the metal is magnetized by the terrestrial magnetism.

12. The apparatus as recited in claim 1, wherein the magnetic flux measuring unit includes numerous magnetic sensors in order to measure a variation of a concentrated magnetic flux density.

13. The apparatus as recited in claim 12, wherein the magnetic sensors are arranged in an array having fixed intervals between adjacent sensors.

14. The apparatus as recited in claim 13, wherein a variation of the magnetic flux density, concentrated by the magnetic flux focusing unit and measured by the magnetic flux density unit, provides measurement of spatial distribution of the magnetic flux density.

15. The apparatus as recited in claim 13, wherein the apparatus amplifies leakage magnetic flux density in a particular region in real time in order to increase a signal to noise (S/N) ratio.

16. A display apparatus of magnetic flux density for detecting an internal crack of a metal or a shape of the metal comprising:
    a three-dimensional magnetic flux focusing unit installed near the metal, for concentrating magnetic flux generated by the metal;
    a magnetic flux density measurement unit installed near the magnetic flux focusing unit, for measuring changes in magnetic flux density concentrated by the magnetic flux focusing unit;
    a display unit electrically connected with the magnetic flux measurement unit, for real-time displaying and storing changes in the magnetic flux density; and
    wherein the magnetic flux focusing unit comprises an absorber of magnetic fluid.

17. The apparatus as claimed in claim 16, wherein the absorber is either one of paper or sponge.

18. A display apparatus of magnetic flux density for detecting an internal crack of a metal or a shape of the metal comprising:
    a first means, near the metal, for concentrating magnetic flux generated by the metal;
    a second means, installed near the first means, for measuring changes in magnetic flux density concentrated by the magnetic flux focusing unit; and
    a third means, connected with the second means, for real-time displaying and storing changes in the magnetic flux density; and
    wherein said first means includes a three-dimensional magnetic fluid and said second means includes a regularly arranged magnetic sensor, wherein the apparatus measures and displays in real time magnetic flux density, amplifying leakage magnetic flux and increasing magnetic flux density in a particular region of the sensor to measure leakage magnetic flux.

* * * * *